(12) United States Patent
Buchner

(10) Patent No.: US 9,066,868 B2
(45) Date of Patent: Jun. 30, 2015

(54) CARNITINE GRANULATE AND METHODS FOR ITS PRODUCTION

(71) Applicant: Lonza Ltd., Basel (CH)

(72) Inventor: Thomas Buchner, Naters (CH)

(73) Assignee: LONZA LTD., Basel (CH)

( * ) Notice: Subject to any disclaimer, the term of this patent is extended or adjusted under 35 U.S.C. 154(b) by 0 days.

(21) Appl. No.: 13/908,645

(22) Filed: Jun. 3, 2013

(65) Prior Publication Data

US 2013/0273165 A1 Oct. 17, 2013

Related U.S. Application Data

(62) Division of application No. 12/964,187, filed on Dec. 9, 2010, now Pat. No. 8,470,382.

(60) Provisional application No. 61/285,805, filed on Dec. 11, 2009.

(30) Foreign Application Priority Data

Dec. 11, 2009 (EP) ..................................... 09015339

(51) Int. Cl.
*A61K 31/205* (2006.01)
*A61K 9/14* (2006.01)
*A23K 1/00* (2006.01)
*A23K 1/16* (2006.01)
*A23L 1/00* (2006.01)
*A23L 1/305* (2006.01)
*A23P 1/02* (2006.01)
*A61K 9/16* (2006.01)

(52) U.S. Cl.
CPC . *A61K 9/14* (2013.01); *A23K 1/002* (2013.01); *A23K 1/1634* (2013.01); *A23K 1/1646* (2013.01); *A23L 1/0017* (2013.01); *A23L 1/3051* (2013.01); *A23P 1/02* (2013.01); *A23V 2002/00* (2013.01); *A61K 9/1611* (2013.01); *A61K 31/205* (2013.01)

(58) Field of Classification Search
CPC ..................................................... A61K 31/205
USPC ........................................... 514/561; 426/648
See application file for complete search history.

(56) References Cited

U.S. PATENT DOCUMENTS

2009/0082449 A1  3/2009  Baumgartner

FOREIGN PATENT DOCUMENTS

EP  0434088  5/1993
JP  0812569  1/1996

*Primary Examiner* — Gina Justice
(74) *Attorney, Agent, or Firm* — Hoffmann & Baron, LLP

(57) ABSTRACT

Subject of the invention is a method for the production of a carnitine granulate, which includes the steps of
(a) providing an aqueous solution comprising at least 65% (w/w) carnitine,
(b) providing a particulate carrier comprising silica, the carrier having an average particle size of more than 150 μm, and
(c) mixing the aqueous solution and the carrier.
Another subject of the invention is a carnitine granulate.

15 Claims, No Drawings

CARNITINE GRANULATE AND METHODS FOR ITS PRODUCTION

CROSS-REFERENCE TO RELATED APPLICATION

This application is a divisional of U.S. application Ser. No. 12/964,187, filed Dec. 9, 2010, which claims priority based on EP Patent Application No. 09015339.6, filed Dec. 11, 2009 and U.S. Provisional Patent Application No. 61/285,805 filed Dec. 11, 2009, both of which are incorporated herein by reference.

The invention relates to carnitine granulates and methods for their production.

BACKGROUND OF THE INVENTION

Carnitine (vitamin BT; 3-hydroxy-4-trimethylammoniobutanoate) is a quaternary ammonium compound biosynthesized from the amino acids lysine and methionine. In living cells, it is required for the transport of fatty acids from the cytosol into the mitochondria during the breakdown of lipids for the generation of metabolic energy. Carnitine exists in two stereoisomers. The biologically active form is L-carnitine, whilst its enantiomer, D-carnitine, is biologically inactive. Pure L-carnitine can be obtained by microbiological processes or by organic synthesis with subsequent purification steps.

Due to its vitamin-like function, L-carnitine has a broad range of pharmaceutical, food and cosmetic applications. L-carnitine is known to have positive effects on energy metabolism and the cardiovascular, muscular and nervous system of humans and animals. L-carnitine is also useful for other purposes, for instance as a nutrient for yeast and bacteria growth. Carnitine can be administered orally to humans and animals.

Solid L-carnitine has a high hygroscopy. Thus powder mixtures have a low stability, in particular storability, and are only of limited use in industry, especially in the food industry.

Various attempts have been made in the art to overcome the problem of hygroscopy. In order to reduce the hygroscopy, EP 0434088 B1 suggests using a salt of L-carnitine with L-tartric acid in the preparation of tablets or capsules.

U.S. 2009/0082449 discloses methods for obtaining carnitine powders or granulates. The carnitine is coated on a solid carrier in order to obtain a coated granulate. In a first method, it is suggested to coat the solid carrier with an aqueous carnitine solution by preparing an aqueous suspension and spray-drying. However, a spray-drying process requires large amounts of water in the spray-drying solution. This is problematic, because the water has to be evaporated subsequently, which requires a large amount of energy and also time. In a second method, it is suggested to mix solid carnitine with a solid carrier. In a third method, a liquid solution of a starting material comprising a low amount of carnitine, such as a permeate or a fermentation product, is mixed with a carrier and subjected to a drying process in order to obtain a granulate. Again, relatively large amounts of water have to be used which subsequently have to be removed in an energy and time consuming process. As outlined in section [0093], the granules tend to form agglomerated particles.

A method for producing granulates coated with carnitine chloride is disclosed in JP 08-012569. According to this method, aqueous solutions comprising usually 30 to 60% by weight carnitine chloride are admixed with carriers which are preferably silica carriers. After drying, the product can be admixed with organic binders and pressed into tablets and the like.

However, the methods known in the art have various drawbacks. At first, removing high amounts of water from a granulate is time and energy consuming. Further, granulates produced by methods in the art usually have a limited flowability. The decrease in flowability over time is indicative of hygroscopy of the carnitine. The flowability of a granulate and the maintenance of the flowability over an extended time period are important product properties. A good flowability is important for handling a granulate, for instance when packaging and proportioning the granulate. Granulates of low flowability tend to stick to surfaces, such as interior surfaces of containers and devices. This is problematic when a granulate is packed and proportioned by mechanical devices. Even further, the hygroscopy is problematic when carnitine or a carnitine granulate is admixed with other components, as for example in feed products for animals. In food products, feed products or feed and food additives, the carnitine is often admixed with other nutrients or other feed or food additives. Due to the hygroscopy of the carnitine, reduced flowability and caking is observed in such mixtures.

Problem Underlying the Invention

The problem underlying the invention is to provide a carnitine granulate and methods for the production of a carnitine granulate, which overcome the above-mentioned problems.

Specifically, the invention shall provide a simple and convenient method for obtaining carnitine granulates. The method shall require a low number or process steps, low amounts of energy, and shall be carried out during a relatively short time span. Energy intensive steps like spray-drying and drying at high temperatures for extended times shall be avoided.

A further problem underlying the invention is to provide a carnitine having a low hygroscopy and high flowability. The carnitine shall be storable for extended time periods without essential deterioration of the material. Specifically, caking of the carnitine shall be reduced or inhibited even over extended time periods. Further, also mixtures of the carnitine with other components, for instance in a feed product, shall have the desired high flowability and low tendency towards caking. It would be of benefit if the carnitine or carnitine formulations can be stored for a longer period of time without using cost intensive special packing to limit or avoid caking.

Another problem underlying the invention is to provide carnitine granulates having a relatively large particle size. This is advantageous, because in general a larger particle size enhances the flowability.

Another problem underlying the invention is to provide a process for preparing a carnitine granulate, in which the dusting of starting products or intermediate products is avoided.

DISCLOSURE OF THE INVENTION

Surprisingly, the problem underlying the invention is solved by the methods, carnitine granulates and uses according to the claims. Further inventive embodiments are disclosed throughout the description.

Subject of the invention is a method for the production of a carnitine granulate, comprising the steps of
(a) providing an aqueous solution comprising at least 65% (w/w) carnitine, (b) providing a particulate carrier comprising silica, the carrier having an average particle size of more than 150 µm, and (c) mixing the aqueous solution and the carrier.

Carnitine is a zwitterion, which comprises a carboxyl group and a quaternary ammonium group. The carnitine comprising solution in step (a) is generally obtainable by dissolving carnitine or a salt thereof in water. The carnitine used for preparing the solution in step (a) is preferably the zwitterionic carnitine. However, it is also possible to use a carnitine salt for preparing the solution, such as a chloride, sulphate or nitrate salt. The carnitine used in step (a) for providing the aqueous solution is preferably not a salt of a carnitine with an optically active anion. According to the invention, a low hygroscopy is obtainable without providing carnitine in the form of a complex salt, for example an organic salt, especially one comprising more than 3 carbon atoms, such as a tartrate or citrate.

The aqueous solution in step (a) comprises at least 65% (w/w), preferably more than 70%, more than 75% or more than 76.5% (w/w) L-carnitine. In preferred embodiments, the solution is close to saturation or a saturated solution or an oversaturated solution. Preferably, the solution is a clear solution.

In general, aqueous solutions comprising such high levels of L-carnitine are obtainable at enhanced temperature. In a preferred embodiment of the invention, the temperature of the aqueous solution is at least 60° C., preferably at least 70° C. or at least 75° C. Preferably, the temperature is between 60 and 90° C., more preferably between 75 and 85° C. It was found that the adjustment of such an enhanced temperature is also advantageous, because the formation of stable granules in step (c) is supported. This might be due to the decreased viscosity of the heated solution. Thus after preparing the aqueous solution in step (a) at an enhanced temperature, it is preferred to mix the solution with the carrier in step (c) at the same or essentially the same temperature, or without cooling the solution in between.

For example, the solution in step (a) is obtained by providing 15 to 35% (w/w) water in a vessel, adding 65 to 85% (w/w) carnitine or a salt thereof and stirring at elevated temperature until the carnitine is dissolved whilst reducing the viscosity of the solution.

In a preferred embodiment, the aqueous solution in step (a) essentially consists of water and carnitine. Impurities, for example side products from the production process may be present. Based on the total amount of solids in the aqueous solution, the level of non-carnitine solids may be below 5%, below 2% or below 1% (w/w). In another embodiment of the invention, the carnitine is used in combination with at least one other soluble component. For example, further active agents might be included, depending on the use of the final product. In a food product, other nutrients could be included, for example vitamins, amino acids, dietary minerals, for example chromium picolinate. In addition or alternatively, auxiliary agents can be included, for example those which enhance the stability or handling of the granulate.

The aqueous solution in step (a) should have a viscosity such that it can be poured or sprayed with common apparatuses. In a preferred embodiment of the invention, the viscosity of the carnitine solution step (a) is between 0.5 to 150 mPas, more preferably between 0.8 and 50 mPas, measured at 70° C., or at the temperature at which solution (a) is prepared.

According to the invention, the average particle diameter of the particulate carrier is above 150 µm, preferably above 180 µm, above 200 µm or above 220 µm. Surprisingly, it was found that stable granulates, which have a high flowability and low hygroscopy, are obtainable when carriers with large particle diameters are used in the specific process of the invention. In a preferred embodiment of the invention, the average particle diameter (d50) of the carrier is between 150 and 1000 µm, more preferably between 180 and 800 µm or between 220 and 500 µm. In a specific preferred embodiment, it was found that an optimal carrier size, especially for a food product or food additive, is between about 200 and about 300 µm. The average particle diameter (d50 µm) can be determined according to ISO 13320:2009. By the method of the invention, also carriers having average particle diameters above 1000 µm can be used, but such products are generally less applicable in pharmaceutical, food or feed applications.

In a preferred embodiment, the ratio of dry carnitine to carrier used as starting compounds in the inventive method is preferably between 0.5:1 and 5:1 or between 1:1 and 2.5:1, more preferably between 1.3:1 and 2:1 (w/w).

In a preferred embodiment of the invention, the BET surface of the carrier is between 100 and 1000 $m^2/g$, more preferably between 150 and 600 $m^2/g$ or between 200 and 500 $m^2/g$ as determined by ISO 5794-1. The BET surface relates to the specific surface of the particles. In general particles having a high BET surface ($m^2/g$) absorb higher amounts of water.

The carrier used according to the invention comprises silica. In a preferred embodiment, the carrier is a microgranulated silica carrier. Microgranulated silica is known in the art and commercially available. Depending on the production process, the particles are usually more or less spherical. According to the invention, the carriers shall be capable of absorbing at least a certain amount of water. Such carriers are commercially available for example under the trademark Tixosil from Rhodia or under the trademark SIPERNAT from Evonik Industries. For example, useful silica carriers according to the invention are Tixosil 68, Tixosil 38X and SIPERNAT 2200, each having an average particle size above 150 µm. Preferably, the silica carrier essentially consists of $SiO_2$. It may comprise minor amounts of impurities due to anions and cations, such as sulphate and sodium, or other metal oxides, such as iron oxide. Usually, the $SiO_2$ content of particles is above 95 or above 98 wt. %. In another embodiment of the invention, the carrier comprises silica in combination with at least one other metal oxide, for example alumina. In these carrier materials, the silica content may be above 10%, above 50% or above 80% (w/w).

In a preferred embodiment of the invention, in step (c) the aqueous solution is fed into a mixer containing the carrier whilst the mixer is agitated. The mixer can be a common device, such as a vertical mixer, vertical screw mixer, paddle mixer, horizontal mixer or spherical mixer. The aqueous solution can be fed into the mixture for example by a spray nozzle or a simple open tube. It is preferred that the feeding of the aqueous solution into the mixer is extended over a certain time interval in order to ensure that the solution is evenly absorbed by the carrier. For example, the feeding of the aqueous solution may be carried out over a period of 20 minutes to 3 hours, preferably between 30 minutes and 2 hours. In general, the feeding speed should be adjusted such that the solution can be absorbed effectively by the carrier in order to obtain a uniform coating. During step (c), the aqueous solution is preferably maintained at an enhanced temperature. Preferably, the temperature or temperature range is selected as in step (a). In addition, the mixer might be heated. The overall process can be carried out as a batch process or as a continuous process.

In a preferred embodiment of the invention, an anticaking agent is added. Anticaking agents are additives which prevent a composition from caking together and thus from forming lumps or a continuous solid. Preferably, an anticaking agent is selected which is acceptable for oral consumption, as necessary in food products or pharmaceuticals. Especially preferred is an anti-caking agent based on silicon dioxide. In order to avoid an interaction of the anticaking agent with the aqueous solution and the product, it is preferred that the anticaking agent is hydrophobic and water-repellent. In a preferred embodiment of the invention, the anticaking agent is hydrophobized silica particles. Preferably, the anticaking agent is a hydrophobized silica granulate, for example with an average particle size below 50 μm, below 30 μm or below 20 μm (d50 as measured by ISO 13320-1). Such products are known in the art and commercially available, for example under the trademark SIPERNAT D17 or SIPERNAT 22 from Evonik Industries. In a preferred embodiment, the amount of anticaking agent added is 0.5 to 10%, more preferably 1 to 5% (w/w) based on the total amount of carrier. Preferably, in the inventive production method the anticaking agent is added after step (c), i.e. after the aqueous solution and the carrier were mixed, or at least after the addition of at least a major portion of the aqueous solution. It was found that the anticaking agent enhances the flowability of the granulate further.

Surprisingly, it was found that the flowability of the final product can be enhanced even further when interrupting the feeding of the aqueous solution whilst continuously agitating the mixture for a certain time. In a preferred embodiment of the invention, in step (c) the aqueous solution is fed into the mixer during at least two time intervals, between which the feeding is interrupted whilst continuously agitating the mixture. Preferably, the aqueous solution is fed into the mixture during two time intervals. Each interval may have a length between 5 minutes to 40 minutes, preferably between 10 minutes to 30 minutes. Preferably, during the first interval 40 to 90%, more preferably 50 to 80% of the aqueous solution is added. In the second interval, the remaining aqueous solution is added. The length of the intermediate interruption may be between 5 to 40 minutes, or between 10 to 30 minutes. The length of the interruption should be sufficient that the carnitine solution in the mixer is absorbed, or essentially absorbed, by the carrier. After adding all the aqueous solution, it is preferred that the mixture is further agitated for a certain time, for instance for at least two minutes, preferably for 3 to 20 minutes.

The length of the time intervals, the amount of aqueous solution added during each interval, the amount of carrier and the velocity of the mixer are interrelated and are adjusted such that the solution is evenly absorbed by the carrier.

In a preferred embodiment of the invention, step (c) comprises the steps of (c1) feeding a first portion of the aqueous solution into the mixer, (c2) agitating the mixture for at least 3 minutes whilst no aqueous solution is fed into the mixer, (c3) feeding a second portion of the aqueous solution into the mixer, (c4) agitating the mixture for at least 3 minutes whilst no aqueous solution is fed into the mixer, wherein optionally an anticaking agent is added after step (c3) or after or during step (c4), wherein the mixer is agitated during steps (c1) to (c4).

The carnitine granulate may be subjected to subsequent processing steps, such as sieving, if desired.

Subject of the invention is also a carnitine granulate, obtainable by a method of the invention. The carnitine granulate is stable and of low hygroscopy.

Another subject of the invention is a carnitine granulate, wherein the granules essentially consist of a silica carrier coated with carnitine. Preferably, the granules have an average particle size of more than 160 μm, or more than 200 μm. For example, the average granule size may be between 200 and 700 μm, or between 220 and 400 μm. The inventive granulate may comprise at least 5% or at least 10% (w/w) carnitine. In a preferred embodiment of the invention, the carnitine granules comprise or essentially consist of between 30 to 95% (w/w) silica carrier and between 70 to 5% (w/w) carnitine, based on the total amount of solids. The carnitine granules may comprise less than 10%, less than 5% or less than 2% (w/w) of other components, for example due to the presence of impurities.

In a preferred embodiment, the granulate mainly comprises single carrier particles with a carnitine coating. The granules are essentially not agglomerates of coated carrier particles. This ensures the uniformity and high flowability of the inventive granulate. In this embodiment, the granulate is thus different from the granulate described in section [0093] of U.S. 2009/0082449, the particles of which are agglomerates of coated carrier particles.

In a preferred embodiment of the invention, the hygroscopy of the granulate is low. The hygroscopy can be determined by the method of ISO 12571:2000.

The granulate of the invention has a good flowability. Preferably, the granulate has a repose angle below 45°, more preferably below 40° or below 35°. The repose angle can be determined by the method of DIN ISO 4324.

In a preferred embodiment of the invention, the carnitine is pure or essentially pure L-carnitine. Small amounts of D-carnitine may be present due to impurities. In a less preferred embodiment, the carnitine may be a racemate or D-carnitine.

Another subject of the invention is the use of a carnitine granulate of the invention in a food, pharmaceutical or cosmetic composition. As used herein, the term "food" refers to any food or feed for humans and animals. The carnitine granulate may be administered to humans or to animals, for example cattle, horses, pigs, poultry, fish or pets, such as cats and dogs.

The carnitine granulate can be admixed with addition compounds. These additional compounds can be substances that are suitable as food ingredients or food additives. In the context of the present invention the term "food ingredient" means a single substance or a mixture of substances which optionally can contain one or more additives and which serve for nutrition of human beings and can be consumed by human beings or animals in an unprocessed, processed and/or formulated state. A "food additive" is a substance that is added to a foodstuff to alter certain features of this foodstuff such as appearance, constitution, consistency, taste, odour, storability, workability etc. or for physiological or nutritional reasons. Examples for food additives include, without being restricted to, sweeteners, bulking agents, flavouring agents, acidifying agents, preservative agents, mineral matter, vitamins, amino acids, antioxidants, enzymes, pigments, emulsifying agents, agents that improve compaction and the like.

The additional compounds can also be substances or substance mixtures that are conventionally used for the preparation of a pharmaceutical composition, without being themselves active ingredients or agents. A "pharmaceutical composition" is a substance or formulation which upon application to or within an animal or human body can cure or heal and/or relieve and/or prevent a certain condition, disease, suffering or injury or which can restore certain functions of a tissue or organ of that body to the normal. Substances which are commonly used for the preparation of pharmaceutical compositions and which are not themselves active agents include, without being restricted to, excipients, lubricants, flavouring agents, disintegrants, binding agents and the like.

The inventive carnitine granulate and the inventive method solve the above mentioned problems. The method of the invention allows the preparation of a carnitine granulate in a relatively simple manner. The inventive method can be carried out whilst consuming low amounts of energy and in a short time, whilst applying simple standard equipment.

In the method of the invention, the process, the solution and the carrier can be adjusted, such that the water used is essentially absorbed by the granules. Thus an energy consuming drying step, such as a spray-drying step, is not necessary. Preferably, the method of the invention does not comprise a spray-drying step. Further, it is not necessary to dry the coated carrier at enhanced temperatures and/or for an extended time. In contrast, when admixing an aqueous solution comprising a high concentration of carnitine at an elevated temperature with a carrier according to the invention, it is possible to obtain a carnitine granulate without subsequent heating and drying steps. Preferably, drying temperatures above 30° C. or above 50° C. and/or drying times above 10 or above 30 minutes are not applied. As used herein, "dry" means that the granules are essentially not wet or moist on the surface. However, they usually have an internal water content, because a portion of the water used in the coating process is adsorbed into the core of the particles.

By the inventive process, a carnitine granulate with highly advantageous properties is obtained. Surprisingly, the carnitine granulate has a low hygroscopy and remains flowable over extended storing time periods. Even when storing the granulate for about 3 months, the flowability is not affected negatively. A carnitine granulate having a high average particle size is obtainable, which improves the flowability.

According to the invention, it is not necessary to introduce stability enhancing additives, such as organic binders, into the granule coatings. In a preferred embodiment, the inventive carnitine granulate essentially consists of the carnitine, the carrier and the anticaking agent, which is preferably silica-based.

WORKING EXAMPLE

Preparation of Aqueous Carnitine Solution

| | |
|---|---|
| 10.5 kg | of water are fed into a stirred vessel. |
| 34.2 kg | of dry carnitine (Levocarnitine) are added in to the vessel.<br>The vessel is heated up to 80° C. and stirred until the solids have been dissolved completely. |

Preparation of Microgranulated Silica

| | |
|---|---|
| 23 kg | of micro granulated silica (Tixosil 68, Rhodia) are fed into a mixer (e.g. Nauta type or horizontal paddle mixer).<br>The mixer is turned on. |

Feeding of Aqueous Carnitine Solution and Mixing

| | |
|---|---|
| | The carnitine solution will be fed at 75 to 80° C. into the running mixer via a spray nozzle or open tube/pipe.<br>In the first feeding step approx. |
| 2/3 | of the aqueous solution are fed in to the mixer within 20 minutes or longer.<br>After completion of the first feeding step the Silica/carnitine/water is mixed for 15 min without feeding of the carnitine/water solution.<br>In the second feeding step the rest of the aqueous solution is fed in to the mixer within 10 minutes or longer. |
| 684 g | of an anti-caking agent (silica) are added at once.<br>After another 7 minutes of mixing time the product is discharged. |
| 67 kg | of granulated carnitine are obtained. |

A granulate with good flowability and low hygroscopicity was obtained. The average particle diameter d50 was about 262 μm. The average particle diameter (d50 μm) was determined according to ISO 13320:2009.

The repose angle of the granulate was determined to be 34.5°, compared to 53.3° of a commercially available feed formulation. The repose angle was determined by the method of DIN ISO 4324.

The HAUSNER ratio was determined to be 1.18 (indicating free flowing), compared to 1.41 (indicating non-flowing) of a commercially available feed formulation. The HAUSNER ratio was determined according to DIN 53194.

The invention claimed is:

1. A carnitine granulate, prepared by the process comprising the steps of
   (a) providing an aqueous solution comprising at least 65% (w/w) carnitine,
   (b) providing a particulate carrier comprising silica, the carrier having an average particle size of more than 150 μm, and
   (c) mixing the aqueous solution and the carrier,
   whereby a drying step is excluded.

2. The carnitine granulate of claim 1, wherein the temperature of the aqueous solution is above 60° C.

3. The carnitine granulate of claim 1, wherein the viscosity of the carnitine solution in step (a) is between 0.5 to 150 mPas.

4. The carnitine granulate of claim 1, wherein the average particle diameter of the carrier is between 150 and 500 μm.

5. The carnitine granulate of claim 1, wherein the BET surface of the carrier is between 100 and 1000 m$^2$/g.

6. The carnitine granulate of claim 1, wherein in step (c) the aqueous solution is fed into a mixer containing the carrier whilst the mixer is agitated.

7. The carnitine granulate of claim 1, wherein an anticaking agent is added.

8. The carnitine granulate of claim 1, wherein the anticaking agent is hydrophobized silica particles.

9. The carnitine granulate of claim 6, wherein in step (c) the aqueous solution is fed into the mixer during at least two time intervals, between which the feeding is interrupted whilst agitating the mixture.

10. The carnitine granulate of claim 1, wherein step (c) comprises the steps of
    (c1) feeding a first portion of the aqueous solution into the mixer,
    (c2) agitating the mixture for at least 3 minutes whilst no aqueous solution is fed into the mixer,
    (c3) feeding a second portion of the aqueous solution into the mixer,
    (c4) agitating the mixture for at least 3 minutes whilst no aqueous solution is fed into the mixer,
    wherein an anticaking agent is added during or after step (c3) or (c4),
    wherein the mixer is agitated during steps (c1) to (c4).

11. A carnitine granulate according to claim 1 having an average particle size of more than 150 μm, wherein the granules essentially consist of a silica carrier coated with carnitine, wherein the granulate optionally comprises an anticaking agent.

12. The carnitine granulate of claim 11, wherein the carnitine granules comprise 30 to 95% (w/w) silica carrier and 70 to 5% (w/w) carnitine, based on the total amount of solids.

13. A carnitine granulate having an average particle size of more than 150 μm, wherein the carnitine granulate has an angle of repose below 35° and a Hausner ratio of not more than 1.18.

14. The carnitine granulate of claim 13, wherein the carnitine granules comprise 30 to 95% (w/w) silica carrier and 70 to 5% (w/w) carnitine, based on the total amount of solids.

15. The carnitine granulate of claim 13, wherein the carnitine granulate comprises an anticaking agent.

* * * * *